(12) United States Patent
Moszner et al.

(10) Patent No.: US 10,130,562 B2
(45) Date of Patent: *Nov. 20, 2018

(54) MONOMER MIXTURE FOR THE PREPARATION OF DENTAL MATERIALS

(71) Applicant: Ivoclar Vivadent AG, Schaan (LI)

(72) Inventors: Norbert Moszner, Mauren (LI); Peter Burtscher, Rankweil (AT); Alexandros Gianasmidis, Balgach (CH)

(73) Assignee: Ivoclar Vivadent AG, Schaan (LI)

( * ) Notice: Subject to any disclaimer, the term of this patent is extended or adjusted under 35 U.S.C. 154(b) by 84 days.

This patent is subject to a terminal disclaimer.

(21) Appl. No.: 15/127,438

(22) PCT Filed: Feb. 26, 2015

(86) PCT No.: PCT/EP2015/000449
§ 371 (c)(1),
(2) Date: Sep. 20, 2016

(87) PCT Pub. No.: WO2015/139811
PCT Pub. Date: Sep. 24, 2015

(65) Prior Publication Data
US 2017/0143592 A1 May 25, 2017

(30) Foreign Application Priority Data
Mar. 20, 2014 (EP) .................................. 14160841

(51) Int. Cl.
*A61K 6/083* (2006.01)
*A61K 6/00* (2006.01)
*A61C 5/70* (2017.01)
*A61C 13/271* (2006.01)
*C08F 22/22* (2006.01)

(52) U.S. Cl.
CPC .............. *A61K 6/083* (2013.01); *A61C 5/70* (2017.02); *A61C 13/26* (2013.01); *A61K 6/0008* (2013.01); *A61K 6/0023* (2013.01); *A61K 6/0073* (2013.01); *A61K 6/0088* (2013.01); *C08F 22/22* (2013.01)

(58) Field of Classification Search
CPC ...................................................... A61K 6/083
See application file for complete search history.

(56) References Cited

U.S. PATENT DOCUMENTS

| 3,084,436 | A | 4/1963 | Landry |
| 3,991,008 | A | 11/1976 | Temin et al. |
| 7,605,190 | B2 | 10/2009 | Moszner et al. |
| 8,829,067 | B2 | 9/2014 | Moszner et al. |
| 9,532,930 | B2* | 1/2017 | Burtscher ............ A61K 6/0052 |
| 2002/0082315 | A1 | 6/2002 | Mosner |
| 2003/0134934 | A1* | 7/2003 | Kojima ................ A61K 6/0023 523/120 |
| 2007/0040151 | A1 | 2/2007 | Etterodt et al. |
| 2008/0076847 | A1 | 3/2008 | Moszner et al. |
| 2010/0068679 | A1 | 3/2010 | Zappini |
| 2010/0240795 | A1 | 9/2010 | Burthscher |
| 2015/0080490 | A1 | 3/2015 | Burtscher et al. |

FOREIGN PATENT DOCUMENTS

| EP | 2233123 A1 | 9/2010 | |
| WO | WO 201315316 A1 * | 10/2013 | ........... A61K 6/0052 |

OTHER PUBLICATIONS

2-Hydroxyethyl methacrylate Safety Data Sheet, Thermo Fisher Scientific, May 24, 2017.*
International Preliminary Report on Patentability of PCT/EP20151000449, dated Sep. 20, 2016, 6 pages.
Mozner, Norbert et al., "A partially aromatic urethane dimethacrylate as a new substitute for Bis-GMA in restorative composites," 2008, pp. 694-699, Dental Materials 24, Elsevier.
Nassiri M Reza et al., "Application of flow cytometry to determine the cytoxicity of urethane dimethacrylate in human cells," 1994, pp. 153-158, Journal of Biomedical Materials Research, vol. 28., John Wiley & Sons, Inc.

* cited by examiner

*Primary Examiner* — Michael F Pepitone
(74) *Attorney, Agent, or Firm* — Ann M. Knab; Thad McMurray

(57) ABSTRACT

Monomer mixture for the preparation of dental materials, which contains at least one low-volatile monomethacrylate, at least one highly viscous polyfunctional methacrylate and at least one low-viscosity polyfunctional methacrylate.

15 Claims, No Drawings

MONOMER MIXTURE FOR THE PREPARATION OF DENTAL MATERIALS

CROSS-REFERENCE TO RELATED APPLICATIONS

This application is a National Stage application of International patent application PCT/EP2015/000449 filed on Feb. 26, 2015, which claims priority to European patent application No. 14160841.4 filed on Mar. 20, 2014, the disclosures of which are incorporated herein by reference in their entirety.

The present invention relates to a monomer mixture for the preparation of dental materials which are suitable in particular for use as dental filling material, dental fixing cement or dental coating material.

Dental composites usually contain a polymerizable organic matrix and one or more fillers. In most cases, a mixture of monomers, initiator components, stabilizers and pigments is used as polymerizable organic matrix, wherein mixtures of dimethacrylates are often used as monomers. Such materials can be cured by thermal, redox-initiated or light-induced radical polymerization. Acidic monomers are also being used increasingly for the preparation of dental materials. These give the materials self-etching properties and improve their adhesion to the natural tooth substance.

Frequently used monomers are dimethacrylates such as 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA), bismethacryloyloxymethyltricyclo[5.2.1.]-decane (TCDMA), decanediol-1,10-dimethacrylate ($D_3MA$) and triethyleneglycol dimethacrylate (TEGDMA). Bis-GMA is the best-known aromatic dimethacrylate, which is also called Bowen's monomer or Bowen's resin after its developer. Bis-GMA has a relatively high viscosity and therefore can be mixed with fillers only with difficulty. It is therefore almost always combined with low-viscosity monomers, wherein a base mixture of bis-GMA with TEGDMA has established itself as the standard for commercial products.

Although bis-GMA and TEGDMA are not systemically toxic, as their $LD_{50}$ values are above 5,000 μg/kg bodyweight (rat), they do show some undesired effects. Bis-GMA and TEGDMA thus have a comparatively high cytotoxicity, and it is known that TEGDMA leads to gene mutations in the DNA molecules of mammals (cf. G. Schmalz, D. Arenholt-Bindslev, Biocompatibility of Dental Materials, Springer-Verlag, Berlin Heidelberg 2009, p. 110 et seq.).

The object of the invention is to provide monomer mixtures for the preparation of dental materials which have low cytotoxicity and are capable of replacing TEGDMA, bis-GMA and mixtures thereof in dental materials. The monomer mixtures are to be characterized by good curing properties, low viscosity, low water-solubility and high reactivity, and make possible the homogeneous incorporation of even large quantities of filler. The mechanical properties of the polymers prepared therefrom are to match those of polymers based on TEGDMA and bis-GMA.

This object is achieved according to the invention by monomer mixtures which contain at least one low-volatile monomethacrylate, at least one highly viscous polyfunctional methacrylate and at least one low-viscosity polyfunctional methacrylate. By monomethacrylates are meant compounds with one, by di- and polyfunctional methacrylates compounds with two or more, preferably 2 to 4, radically polymerizable groups. Monomer mixtures are preferred which contain at least one low-volatile monomethacrylate, at least one highly viscous difunctional methacrylate and at least one low-viscosity difunctional methacrylate.

According to the invention by low-volatile monomers are meant compounds with a boiling point >150° C. at normal pressure. The boiling point can e.g. be determined using a distillation apparatus. By highly viscous monomers are meant substances with a viscosity ≥5 Pa·s, preferably from 5 to 10,000 Pa·s and particularly preferably from 5 to 2,000 Pa·s and by low-viscosity monomers are meant substances with a viscosity ≤300 mPa·s, preferably from 1 to 300 mPa·s and particularly preferably from 30 to 300 mPa·s, wherein the viscosity is determined using a capillary viscometer (low viscosity) or rotating viscometer (high viscosity) at a temperature of 25° C.

The radically polymerizable monomer mixture according to the invention preferably contains:
from 2 to 50 wt.-%, particularly preferably from 5 to 45 wt.-% and quite particularly preferably from 10 to 30 wt.-% of at least one low-volatile monomethacrylate;
from 5 to 65 wt.-%, particularly preferably from 8 to 60 wt.-% and quite particularly preferably from 25 to 50 wt.-% of at least one highly viscous polyfunctional, preferably difunctional, methacrylate; and
from 5 to 55 wt.-%, particularly preferably from 10 to 50 wt.-% and quite particularly preferably from 20 to 45 wt.-% of a low-viscosity polyfunctional, preferably difunctional, methacrylate.

The above values by weight relate to the total mass of the monomer mixture.

Particularly preferred highly viscous dimethacrylates are TMX-UDMA (an addition product of HEMA and hydroxypropyl methacrylate (HPMA) with α,α,α',α'-tetramethyl-m-xylylene diisocyanate (TMXDI)) and 1,6-bis-[2-methacryloyloxyethoxycarbonylamino]-2,4,4-trimethylhexane (UDMA). Preferred low-viscosity dimethacrylates, which are used as diluting monomers, are bismethacryloyloxymethyltricyclo-[5.2.1.]decane (TCDMA), glycerol dimethacrylate (GDMA) and in particular decanediol-1,10-dimethacrylate ($D_3MA$). A particularly preferred low-volatile monomethacrylate is p-cumylphenoxyethylene glycol methacrylate (CMP-1E).

A monomer mixture which contains 20 wt.-% CMP-1E, 20 wt.-% GDMA, 20 wt.-% TMX-UDMA, 25 wt.-% UDMA and 15 wt.-% $D_3MA$ has proved particularly worthwhile.

The monomer mixture according to the invention is particularly suitable for the preparation of dental materials, in particular of filling composites, fixing cements and dental coating materials, such as e.g. fissure sealants. The monomer mixtures and dental materials according to the invention do not contain any TEGDMA and preferably also do not contain any bis-GMA. In the following, by dental materials are meant compositions which, in addition to the monomer mixture defined above, contain at least one further component, preferably at least one initiator for the radical polymerization, particularly preferably a photoinitiator.

It was surprisingly found that the monomer mixtures according to the invention can replace TEGDMA, bis-GMA and mixtures thereof in dental materials without impairing the curing behaviour, the mechanical properties or the functional substances of the materials. The monomer mixture according to the invention is characterized by a lower cytotoxicity compared with TEGDMA and bis-GMA.

To prepare dental materials, further radically polymerizable monomers can be added to the above monomer mixture according to the invention.

As additional radically polymerizable monomers or mixtures of radically polymerizable monomers, methacrylates are preferred, mixtures of mono- and polyfunctional methacrylates are particularly preferred, and mixtures of mono- and difunctional methacrylates are quite particularly preferred.

Preferred mono- or polyfunctional methacrylates are methyl, ethyl, 2-hydroxyethyl, butyl, benzyl, tetrahydrofurfuryl or isobornyl(meth)acrylate, ethoxylated or propoxylated bisphenol A dimethacrylate, such as e.g. the bisphenol A dimethacrylate SR-348c with 3 ethoxy groups or 2,2-bis [4-(2-methacryloxypropoxy)phenyl]propane, di-, tri- or tetraethylene glycol dimethacrylate, trimethylolpropane trimethacrylate, pentaerythritol tetramethacrylate, as well as glycerol di- and trimethacrylate, 1,4-butanediol dimethacrylate, or 1,12-dodecanediol dimethacrylate.

Alternatively or in addition, the monomer mixture according to the invention can contain, in addition to the monomers named above one or more acid-group-containing radically polymerizable monomers (adhesive monomers) as additional monomers. These give the materials self-adhesive and/or self-etching properties.

Preferred acid-group-containing monomers are polymerizable carboxylic acids, phosphonic acids, phosphoric acid esters, and sulphonic acids.

Preferred carboxylic acids are maleic acid, acrylic acid, methacrylic acid, 2-(hydroxymethyl)acrylic acid, 4-(meth)acryloyloxyethyl trimellitic acid, 10-methacryloyloxy-decylmalonic acid, N-(2-hydroxy-3-methacryloyloxypropyl)-N-phenylglycine and 4-vinylbenzoic acid.

Preferred phosphonic acid monomers are vinylphosphonic acid, 4-vinylphenylphosphonic acid, 4-vinylbenzylphosphonic acid, 2-methacryloyloxyethylphosphonic acid, 2-methacrylamidoethyl-phosphonic acid, 4-methacrylamido-4-methylpentylphosphonic acid, 2-[4-(dihydroxyphosphoryl)-2-oxa-butyl]-acrylic acid or 2-[4-(dihydroxyphosphoryl)-2-oxa-butyl]-acrylic acid ethyl and -2,4,6-trimethylphenyl ester.

Preferred acidic polymerizable phosphoric acid esters are 2-methacryloyloxypropyl mono- or dihydrogen phosphate, 2-methacryloyloxyethyl mono- or dihydrogen phosphate, 2-meth-acryloyloxyethylphenyl hydrogen phosphate, dipentaerythritol-pentamethacryloyloxyphosphate, 10-methacryloyloxydecyl dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl-dihydrogen phosphate.

Preferred polymerizable sulphonic acids are vinyl sulphonic acid, 4-vinylphenyl sulphonic acid or 3-(methacrylamido)propyl sulphonic acid.

Particularly preferred adhesive monomers are 4-(meth)acryloyloxyethyl trimellitic acid, 2-[4-(dihydroxyphosphoryl)-2-oxa-butyl]-acrylic acid ethyl or -2,4,6-trimethylphenyl ester and 10-methacryloyloxydecyl dihydrogen phosphate.

According to an embodiment of the invention the dental materials contain no further monomers in addition to the monomer mixture according to the invention.

The monomer mixtures according to the invention preferably also contain an initiator for the radical polymerization. To cure the materials, e.g. in the case of indirect filling materials, thermal initiators, such as e.g. dibenzoyl peroxide (DBPO), or derivatives of barbituric acid, such as e.g. trimethylbarbituric acid, are used. For curing at room temperature, the peroxides are combined with amines such as N,N-dimethyl-sym.-xylidine or N,N-dimethyl-p-toluidine and the barbituric acid derivatives are combined with percompounds such as e.g. potassium peroxosulphate or peresters.

α-Diketones such as e.g. camphorquinone (1,7,7-trimethylbicyclo[2.2.1]heptane-2,3-dione) (CQ) and 9,10-phenanthrenequinone are preferred as photoinitiators for light-curing materials. Preferably, photoinitiators are used together with amines such as 4-(N,N-dimethylamino)benzoic acid ethyl ester as reducing agent. Dual-curing dental materials contain a mixture of a photoinitiator and a redox-initiator system.

According to the invention, dental materials are preferred which contain a combination of at least one thiourea derivative and at least one bisacyldialkylgermanium compound as initiator for the radical polymerization. This initiator system makes it possible to prepare materials which are storage-stable, in particular even in the presence of acidic components, which have improved mechanical properties and are colour-stable after curing. Dual-curing dental materials contain, furthermore, a peroxide, preferably a hydroperoxide, as additional initiator component.

Thiourea derivatives which are preferred according to the invention are described in U.S. Pat. No. 3,991,008 (column 2, line 35 to column 3, line 14) and in EP 1 754 465 A1 (paragraph [0009]). Particularly preferred thiourea derivatives are methyl, ethyl, allyl, butyl, hexyl, octyl, benzyl, 1,1,3-trimethyl, 1,1-diallyl, 1,3-diallyl, 1-(2-pyridyl)-2-thiourea, acetyl, propanoyl, butanoyl, pentanoyl, hexanoyl, heptanoyl, octanoyl, nonanoyl, decanoyl and benzoyl thiourea, wherein acetyl and hexanoyl thiourea are quite particularly preferred.

Preferred bisacyldialkylgermanium compounds are described in EP 1 905 413 A1, EP 1 905 415 A1 and EP 2 103 297 A1, wherein bisacylgermanes according to Formula (II) of EP 1 905 413 A1 are particularly preferred. Quite particularly preferred bisacyldialkylgermanium compounds are bisbenzoyldiethylgermanium, bisbenzoyldimethylgermanium, bisbenzoyldibutylgermanium, bis(4-methoxybenzoyl)dimethylgermanium and bis(4-methoxybenzoyl) diethylgermanium, wherein bis(4-methoxybenzoyl) diethylgermanium is most preferred.

Preferred hydroperoxides are 1,1,3,3-tetramethylbutyl hydroperoxide, t-butyl hydroperoxide, cumene hydroperoxide, pinane hydroperoxide, p-menthane hydroperoxide, diisopropylbenzene hydroperoxide and t-amyl hydroperoxide, wherein cumene hydroperoxide is particularly preferred.

Photopolymerizable dental materials are preferably present as single-component systems, i.e. in the form of a mixture which contains all the constituents of the dental material. As initiator they contain exclusively a photoinitiator and can be cured by irradiation with light.

In addition to the photoinitiator, dual-curing dental materials additionally contain a peroxide, preferably a hydroperoxide, as oxidizing agent. Dual-curing materials are preferably present in the form of two separate components, as otherwise a premature curing would take place, wherein the first component contains the (hydro)peroxide and the second component contains the thiourea derivative. The thiourea derivative serves as reducing agent (accelerator). The components are correspondingly also called catalyst paste and accelerator paste.

The curing of the dual-curing materials can be activated by mixing the catalyst and accelerator pastes. The composition is adjusted such that it still remains processable for a few minutes after the pastes are mixed (so-called processing time), but cures rapidly after the processing. The processing and curing times can be adjusted primarily through the type and concentration of (hydro)peroxide, thiourea derivative and optionally by the addition of further components such as a transition metal redox catalyst and inhibitor.

As a rule, a polymerization activated by redox initiator systems proceeds more slowly than a photopolymerization. Correspondingly, excesses can be removed easily in the case of dual-curing materials, by the radiation-activated photopolymerization only taking place after excesses have been removed.

Furthermore, the dental materials according to the invention preferably also contain organic or particularly preferably inorganic particulate fillers. Fillers based on oxides are preferred, such as $SiO_2$, $ZrO_2$ and $TiO_2$ or mixed oxides of $SiO_2$, $ZrO_2$, ZnO and/or $TiO_2$, nanoparticulate or microfine fillers such as pyrogenic silicic acid or precipitated silicic acid (weight-average particle size of 10-1,000 nm) as well as mini fillers, such as quartz, glass ceramic or X-ray opaque glass powder e.g. from barium or strontium aluminium silicate glasses (weight-average particle size of 0.2-10 μm). Further preferred fillers are X-ray opaque fillers, such as ytterbium trifluoride or nanoparticulate tantalum(V) oxide or barium sulphate or mixed oxides of $SiO_2$ with ytterbium (III) oxide or tantalum(V) oxide (weight-average particle size of 10-1,000 nm).

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane. For the surface-modification of non-silicate fillers, e.g. of $ZrO_2$ or $TiO_2$, functionalized acidic phosphates such as e.g. 10-methacryloyloxy dihydrogen phosphate can also be used.

Dental materials containing filler are particularly suitable as dental filling composites, cements and coating materials. Materials are particularly preferred which only contain fillers with a maximum particle size of less than 600 nm. These are particularly suitable as dental cements.

Optionally, the compositions used according to the invention can contain further additives, above all stabilizers, such as e.g. polymerization stabilizers, dyes, microbiocidal active ingredients, fluoride-ion-releasing additives, optical brighteners, fluorescent agents, plasticizers, transition metal redox catalysts and/or UV absorbers.

Compounds of transition metals which have at least two stable valency stages are particularly suitable as transition metal redox catalysts. They are, above all, compounds of the elements copper, iron, vanadium, nickel or cobalt, wherein copper compounds are particularly preferred and these are quite particularly preferably used as highly organosoluble compounds, such as e.g. as acetylacetonate, naphthenate or 2-ethylhexanoate. These catalysts accelerate the redox reaction of oxidizing and reducing agents and thus the formation of radicals, i.e. e.g. the redox reaction of hydroperoxide and thiourea derivative.

According to the invention, those dental materials which have the following composition are particularly preferred:
(a) 12.0 to 75 wt.-%, particularly preferably 19 to 56 wt.-% of the monomer mixture according to the invention,
(b) 20 to 85 wt.-%, particularly preferably 40 to 80 wt.-% filler(s),
(c) 0.05 to 4 wt.-%, preferably 0.1 to 2.0 wt.-% initiator for the radical polymerization and optionally
(d) 0.1 to 5.0 wt.-%, particularly preferably 0.1 to 2.0 wt.-% additive(s).

The above values relate to the total mass of the dental material.

The dental materials according to the invention contain as component (c) preferably from 0.01 to 4.0 wt.-%, particularly preferably from 0.1 to 2.0 wt.-% thiourea derivative(s) and from 0.001 to 1.0 wt.-%, particularly preferably from 0.005 to 0.5 wt.-% bisacyldialkylgermanium compound(s). Dual-curing materials preferably additionally contain from 0.1 to 3.0 wt.-%, particularly preferably from 0.1 to 2.0 wt.-% hydroperoxide(s).

The dental materials according to the invention can contain as component (e) from 0 to 15 wt.-%, particularly preferably 0-10 wt.-% of one or more acid-group-containing adhesive monomers.

The dental materials according to the invention can be provided in a one- or two-component form. Dual-curing materials preferably have two components, i.e. they contain two separate components which are mixed with one another before being used. The composition of the components is chosen such that, after mixing, materials with the total composition defined above are obtained.

Those dental materials that consist of the named substances are particularly preferred. Furthermore preferred are those materials in which the individual substances in each case are selected from the above-named preferred and particularly preferred substances. Materials are quite particularly preferred which do not contain any amines such as e.g. amine accelerators.

The dental materials according to the invention are particularly suitable as dental cements, filling composites, coating and veneering materials as well as materials for preparing inlays, onlays, crowns and bridges. The materials preferably only contain fillers with a maximum particle size of <600 nm. They permit the preparation of dental materials with low surface roughness and high gloss as well as excellent abrasion stability.

The dental materials are suitable primarily for intraoral use by the dentist to restore damaged teeth (clinical materials). However, they can also be used extraorally, for example in the preparation or repair of dental restorations (technical materials).

The invention is explained in more detail below by means of embodiment examples.

EMBODIMENT EXAMPLES

Examples 1-3

Light-Curing Composites Based on a Monomer Mixture According to the Invention

Corresponding to Table 1 set out below, composites were prepared (all values given in mass-%) based on 44.5% of a silanized $SiO_2$ mixed oxide with a content of 30 wt.-% $ZrO_2$ and 20% ytterbium fluoride. In the examples, a monomer mixture according to the invention (20% CMP-1E, 20% GDMA, 20% TMX-UDMA, 25% UDMA and 14.5% $D_3MA$ as well as 0.5% BHT as stabilizer) was used on the one hand and, as a comparison, a monomer mixture based on bis-GMA and TEGDMA (20% bis-GMA, 20% TEGDMA, 20% CMP-1E, 25% UDMA and 14.5% $D_3MA$ as well as 0.5% BHT as stabilizer) was used. The components given in Table 1 were contained as initiator system. The composites were prepared using a kneader (Linden).

The mechanical properties of the materials were then determined. The bending strength (BS) and the elastic modulus (EM) were measured according to the standard ISO 4049 (Dentistry—Polymer-based filling, restorative and luting materials). The measured values are given in Table 2.

To measure the Vickers hardness (VH), metal moulds (h=2 mm, Ø=10 mm) were filled with composite and covered with a PET film. The polymerization was carried out by irradiation from above with a polymerization lamp (LED Bluephase; Ivoclar Vivadent AG; 10 s at 650 mW/cm$^2$). After preparation, the test pieces were stored in a drying oven at 37° C. for 24 h and then the illuminated upper side of the test pieces was ground flat first with a 2500, then with a 4000 abrasive paper and finally polished with polishing paste. The Vickers hardness was measured on the polymerized upper side with a universal hardness tester (model ZHU0.2; Zwick/Röll). 3 individual measurements were carried out on each test piece. The resulting average values are given in Table 2.

The results demonstrate that the monomer mixtures according to the invention make it possible to prepare dental materials which have similar properties to materials based on the proven monomers bis-GMA/TEGDMA. Composites which contain a Ge photoinitiator (Ivocerin®) in combination with a thiourea derivative have a significantly increased Vickers hardness compared with composites which contain camphorquinone in combination with an amine accelerator (EMBO).

TABLE 1

Dental composites (values given in wt.-%)

| Component | Ex. 1 | Ex. 2 | Ex. 3*) |
|---|---|---|---|
| Monomer mixture | 33.95 | 35.45 | 35.45 |
| SiO$_2$ mixed oxide[1)] | 44.5 | 44.5 | 44.5 |
| YbF$_3$ | 20 | 20 | 20 |
| Ivocerin ®[2)] | 0.05 | — | — |
| ATU[3)]/Cu[4)] | 1.50 (65 ppm) | — | — |
| CQ[5)] | — | 0.02 | 0.02 |
| EMBO[6)] | — | 0.03 | 0.03 |

*)Comparison example
[1)]SiO$_2$ with a content of 30 wt.-% ZrO$_2$
[2)]Bis(4-methoxybenzoyl)diethylgermanium (photoinitiator, Ivoclar Vivadent)
[3)]1-Acetylthiourea (accelerator)
[4)]Cu-acetylacetonate (Cu content in ppm)
[5)]Camphorquinone (photoinitiator)
[6)](4-Dimethylamino) benzoic acid ethyl ester (amine accelerator)
[7)]Stabilizer

TABLE 2

Mechanical properties of the composites

| Ex. | Bending strength [MPa] | Elastic modulus [MPa] | Vickers hardness (MPa) |
|---|---|---|---|
| 1 | 91.0 ± 7.9 | 4870 ± 197 | 242.8 ± 10.1 |
| 2 | 98.7 ± 7.9 | 4910 ± 268 | 207.7 ± 7.7 |
| 3*) | 105 ± 5.5 | 5120 ± 152 | 198.4 ± 10.0 |

*)Comparison example

The invention claimed is:

1. A monomer mixture for the preparation of dental materials which comprises
at least one low-volatile monomethacrylate,
at least one highly viscous polyfunctional methacrylate and
at least one low-viscosity polyfunctional methacrylate,
wherein the at least one highly viscous polyfunctional methacrylate comprises 20 wt.-% TMX-UDMA (an addition product of HEMA and hydroxypropyl methacrylate (HPMA) with α,α,α',α'-tetramethyl-m-xylylene diisocyanate (TMXDI)) and 25 wt.-% 1,6-bis-[2-methacryloyloxyethoxycarbonylamino]-2,4,4-trimethylhexane (UDMA),
wherein the at least one low-viscosity polyfunctional methacrylate comprises 20 wt.-% glycerol dimethacrylate (GDMA) and 15 wt.-% decanediol-1,10-dimethacrylate (D3MA) and
wherein the at least one low-volatile monomethacrylate comprises 20 wt.-% p-cumylphenoxyethylene glycol methacrylate (CMP-1E) and
wherein all percentages relate to the total mass of the monomer mixture.

2. The monomer mixture according to claim 1, in which the low-volatile monomer(s) has/have a boiling point >150° C. at normal pressure, the highly viscous monomer(s) has/have a viscosity >5 Pa s (measured using a capillary viscometer at 25° C.) and the low-viscosity monomer(s) has/have a viscosity <300 mPa s (measured using a rotating viscometer at 25° C.).

3. The monomer mixture according to claim 1, which does not contain any TEGDMA and also does not contain any bis-GMA.

4. The monomer mixture according to claim 1, which additionally comprises an initiator for radical polymerization comprising a combination of a thiourea derivative and a bisacyldialkylgermanium compound.

5. The monomer mixture according to claim 4, which comprises as the thiourea derivative, methyl, ethyl, allyl, butyl, hexyl, octyl, benzyl, 1,1,3-trimethyl, 1,1-diallyl, 1,3-diallyl, 1-(2-pyridyl)-2-thiourea, acetyl, propanoyl, butanoyl, pentanoyl, hexanoyl, heptanoyl, octanoyl, nonanoyl, decanoyl, benzoyl thiourea or a mixture thereof.

6. The monomer mixture according to claim 5, which comprises as the bisacyldialkylgermanium compound, bis-benzoyldiethylgermanium, bisbenzoyldimethylgermanium, bisbenzoyldibutylgermanium, bis(4-methoxybenzoyl)dimethylgermanium, bis(4-methoxybenzoyl)diethylgermanium or a mixture thereof.

7. The monomer mixture according to claim 6, which additionally comprises a peroxide or a hydroperoxide.

8. The monomer mixture according to claim 7, which comprises as hydroperoxide, 1,1,3,3-tetramethylbutyl hydroperoxide, t-butyl hydroperoxide, cumene hydroperoxide, pinane hydroperoxide, p-menthane hydroperoxide, diisopropylbenzene hydroperoxide, t-amyl hydroperoxide or a mixture thereof.

9. The monomer mixture according to claim 1, which additionally comprises organic or inorganic particulate filler.

10. The monomer mixture according to claim 9, which only comprises filler with a maximum particle size of less than 600 nm.

11. The monomer mixture according to claim 1, which comprises
(a) 12-75 wt.-% of the monomer mixture,
(b) 20-85 wt.-% filler(s),
(c) 0.05-4 wt.-% initiator for the radical polymerization and optionally
(d) 0.1-5.0 wt.-% additive(s).

12. Method of using the monomer mixture according to claim 1 as dental cement, filling composite, coating material, veneering material, as materials for preparing inlays, onlays, crowns or bridges comprising
preparing the ingredients comprising 12-75 wt.-% of the monomer mixture, 20-85 wt.-% filler(s), 0.05-4 wt.-% initiator for the radical polymerization and optionally 0.1-5.0 wt.-% additive(s), and applying the ingredients as a dental cement, filling composite, coating material, veneering material, inlay, onlay, crown or bridge.

13. The monomer mixture according to claim 1, which comprises
   from 5 to 45 wt.-% of at least one low-volatile monomethacrylate;
   from 8 to 60 wt.-% of at least one highly viscous polyfunctional methacrylate; and
   from 10 to 50 wt.-% of a low-viscosity polyfunctional, methacrylate.

14. The monomer mixture according to claim 1, which comprises
   from 10 to 30 wt.-% of at least one low-volatile monomethacrylate;
   from 25 to 50 wt.-% of at least one highly viscous difunctional, methacrylate; and
   from 20 to 45 wt.-% of a low-viscosity difunctional methacrylate.

15. The monomer mixture according to claim 1, which comprises
   (a) 19-56 wt.-% of the monomer mixture,
   (b) 40-80 wt.-% filler(s),
   (c) 0.1-2.0 wt.-% initiator for the radical polymerization and optionally
   (d) 0.1-2.0 wt.-% additive(s).

* * * * *